United States Patent [19]

Baschang et al.

[11] 4,177,344
[45] Dec. 4, 1979

[54] ANHYDRO-SUGARS

[75] Inventors: Gerhard Baschang, Bettingen; Jaroslav Stanek, Birsfelden; Alberto Rossi, Oberwil; Alex Sele, Muttenz, all of Switzerland

[73] Assignee: Ciba-Geigy Corporation, Ardsley, N.Y.

[21] Appl. No.: 833,795

[22] Filed: Sep. 16, 1977

[30] Foreign Application Priority Data

Sep. 29, 1976 [CH] Switzerland .................. 12299/76

[51] Int. Cl.² .............................................. C07H 3/10
[52] U.S. Cl. ...................................... 536/4; 424/180; 536/1; 536/119; 536/120
[58] Field of Search ...................... 536/4, 119, 120, 1

[56] References Cited

U.S. PATENT DOCUMENTS

| 3,305,542 | 2/1967 | Carlberg et al. | 536/120 |
| 3,414,560 | 12/1968 | Carlberg et al. | 536/120 |
| 3,914,212 | 10/1975 | Baschang et al. | 536/4 |

OTHER PUBLICATIONS

"Advances in Carbohydrate Chemistry", vol. 23, 1968, pp. 437–442.
"Advances in Carbohydrate Chemistry", vol. 26, 1971, pp. 55–60.

Primary Examiner—Johnnie R. Brown
Attorney, Agent, or Firm—John J. Maitner

[57] ABSTRACT

The invention relates to novel 1,6-anhydro-β-D-hexopyranose derivatives of the formula I

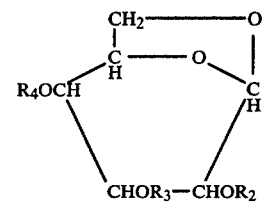

in which $R_2$ is hydrogen, methyl or aromatic acyl, $R_3$ and $R_4$ are alkyl, alkenyl or aralkyl and one of the radicals $R_3$ and $R_4$ is also an aroyl radical and $R_4$ can also be hydrogen, with the proviso that the radicals $R_3$ and $R_4$ together contain at least 3 carbon atoms and, if $R_4$ is the benzyl radical, the radical $R_3$ contains at least 2 carbon atoms, and, if one of the radicals $R_3$ and $R_4$ is an aroyl radical, $R_2$ is hydrogen.

These compounds especially the 1,6-anhydro-3,4-di-O-benzyl-β-D-glucopyranose or the 1,6-anhydro-β-D-glucopyranose, can be used as fibrinolytic agents and thrombolytic agents.

7 Claims, No Drawings

ANHYDRO-SUGARS

The invention relates to novel 1,6-anhydro-β-D-hexopyranose derivatives of the formula I

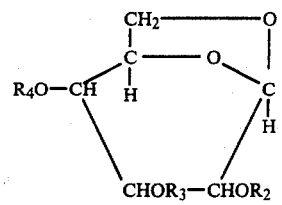

in which $R_2$ is hydrogen, methyl or aromatic acyl, $R_3$ and $R_4$ are an alkyl, alkenyl or aralkyl radical and one of the two radicals $R_3$ and $R_4$ is also an aroyl radical and $R_4$ can also be hydrogen, with the proviso that the radicals $R_3$ and $R_4$ together contain at least 3 carbon atoms and, if $R_4$ is the benzyl radical, the radical $R_3$ contains at least 2 C atoms and, if one of the radicals $R_3$ and $R_4$ is an aroyl radical, $R_2$ is hydrogen, and a process for their preparation.

The novel anhydropyranose derivatives of the formula I belong to the altro, gulo, ido or talo, especially the allo, galacto or manno and, in particular, the gluco series.

In the text which follows, lower radicals are especially those with 1–7 C atoms and in particular with up to 4 C atoms.

Alkyl is especially lower alkyl, for example ethyl, iso-propyl, straight-chain or branched butyl, pentyl, hexyl or heptyl, which are bonded in any desired position, and in particular methyl or n-propyl.

Alkenyl is especially lower alkenyl, for example isopropenyl, 2-methallyl, 3-butenyl and, in particular, allyl.

Aralkyl is especially aryl-lower alkyl in which the lower alkyl part is, in particular, as defined above and especially is methyl and in which the aryl part is 1- or 2-naphthyl or, in particular, phenyl, these radicals being unsubstituted or substituted, such as by halogen, especially bromine and in particular chlorine, lower alkyl, lower alkoxy, trifluoromethyl and/or hydroxyl, and the aryl part carrying several substituents, such as two or three but preferably one, especially in the 4-position, or being unsubstituted.

Lower alkoxy radicals which may be mentioned are especially ethoxy and propoxy, iso-propoxy or, in particular, methoxy radicals.

Aroyl is an acyl radical of an organic aromatic carboxylic acid, such as naphthoyl-1 or naphthoyl-2 and especially benzoyl or benzoyl substituted by halogen, lower alkyl, lower alkoxy, trifluoromethyl, hydroxyl or lower alkanoyl, such as salicyloxyl or o-acetylsalicyloyl, and also pyridylcarbonyl, for example nicotinoyl.

Acyl is, however, also an acyl radical of a carboxylic acid having an anti-inflammatory action, especially an acyl radical of the formula II

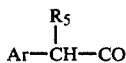

in which $R_5$ is a hydrogen atom or a lower alkyl radical, especially the methyl radical, and Ar is a phenyl or naphthyl radical which can preferably be substituted by cycloalkyl, cycloalkenyl, aryl, lower alkyl, lower alkoxy, phenoxy, halogen, pyrrolino and/or hydroxyl groups.

As a substituent of the phenyl radical Ar, cycloalkyl is, for example, monocyclic, bicyclic or polycyclic cycloalkyl having, for example, up to 12, such as 3–8 and preferably 5–8, ring carbon atoms, especially cyclopentyl or cyclohexyl.

As a substituent of the phenyl radical Ar, cycloalkenyl is, for example, a monocyclic cycloalkenyl having 3–8 and preferably 5–8 ring carbon atoms, especially cyclohexenyl or cyclopentenyl.

As a substituent of the radical Ar, lower alkyl is especially the lower alkyl indicated for $R_2$, in particular methyl.

Cycloalkyl $R_5$ or $R_6$ is especially as defined for cycloalkyl substituents of the radical Ar and is, in particular, cyclopropyl, cyclobutyl, cyclopentyl or cyclohexyl.

Aryl-lower alkyl $R_5$ or $R_6$ is, in particular, benzyl or 2-phenylethyl.

The novel compounds possess valuable pharmacological properties.

Thus, the anhydropyranose derivatives according to the invention show, especially, fibrinolytic and thrombolytic actions, as can be shown in animal experiments, for example on oral administration of about 0.1 to about 5 mg/kg and especially of about 0.3 to about 3 mg/kg to rats in the kaolin paw oedema test. The fibrinolytic and thrombolytic activity also manifests itself in an experiment on normal rats in accordance with the publication by M. Ruegg, L. Riesterer and R. Jaques, Pharmacology, 4, 242–254 (1970), in a shortening of the euglobulin clot lysis time with a dose of 3 to 30 mg/kg.

With regard to their activity, compounds of the formula

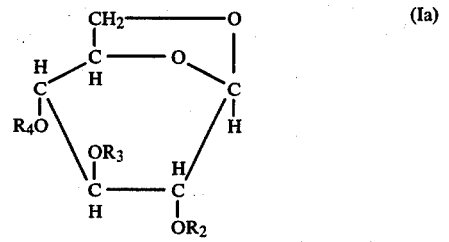

in which $R_2$, $R_3$ and $R_4$ are as defined above, and also the corresponding galacto derivatives are to be singled out in particular.

Compounds of the formula (Ia) and the corresponding galacto derivatives, in which $R_2$ is hydrogen or a lower alkanoyl or aroyl radical and $R_3$ is a lower alkyl or aryl-lower alkyl radical and $R_4$ is hydrogen or a lower alkyl, aryl-lower alkyl or aroyl radical, with the proviso that the radicals $R_3$ and $R_4$ together contain at least 3 carbon atoms and, if $R_4$ is the benzyl radical, the radical $R_3$ contains at least 2 carbon atoms and, if $R_4$ is an aroyl radical, $R_2$ is hydrogen, show particularly favourable activity.

Those compounds of the formula (Ia), and their corresponding galacto derivatives, in which $R_3$ is a benzyl radical and $R_2$ and $R_4$ are as defined above and, in particular, $R_2$ is hydrogen or lower alkyl and $R_4$ is hydrogen or benzyl, with the proviso that, if $R_4$ is an aroyl radical, $R_2$ is hydrogen, are to be singled out in particular.

Their activity can be shown in the kaolin paw oedema test on rats on oral administration, in which test, for example, 1,6-anhydro-3,4-di-O-benzyl-β-D-glucopyranose or 1,6-anhydro-3-O-benzyl-β-D-glucopyranose in doses of 0.3 to 3 mg/kg effect a pronounced shortening of the euglobulin clot lysis time.

The novel compounds can therefore be used as fibrinolytic agents and thrombolytic agents.

The novel compounds which contain an acyl radical of the formula II of a carboxylic acid having an anti-inflammatory action, as the radical $R_2$, additionally show novel anti-inflammatory and antinociceptive (analgesic) actions coupled with low toxicity. Thus, in the adjuvant-arthritis test [based on the procedure described by Newbould, Brit. J. Pharmacol., volume 21, pages 127–136 (1936)] on rats, these novel compounds show pronounced anti-inflammatory actions on oral administration. The novel compounds can therefore also be used as compounds having an anti-inflammatory (antiphlogistic), for example antiexudative or vascular permeability-inhibiting action and in particular as compounds having an anti-arthritic and analgesic action, especially for the treatment of inflammations of a rheumatic nature.

The novel anhydropyranoses can be prepared according to methods which are known per se.

Thus, the novel anhydropyranose derivatives can be prepared by treating a compound of the formula III

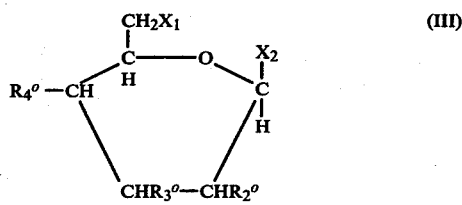

in which $R_2°$, $R_3°$ and $R_4°$ have the meanings defined for the radicals $OR_2$, $OR_3$ and $OR_4$ but can also be a protective group and one of the radicals $X_1$ and $X_2$ is a radical which can be split leaving behind a negatively charged oxygen atom and the other is a radical which can be detached leaving behind a carbonium ion, with acids or bases and detaching any protective group which may be present.

A radical $X_1$ or $X_2$ which can be split leaving behind a negatively charged oxygen atom is, especially, the hydroxyl group.

A radical $X_1$ which can be split leaving behind a negatively charged oxygen atom is also, especially, reactive etherified hydroxyl, such as, in particular, arylmethoxy, such as lower alkyl-benzyloxy, lower alkoxybenzyloxy, halogenobenzyloxy and especially benzyloxy, trityloxy or diphenylmethoxy, or also organosilyloxy, for example trimethylsilyloxy.

A radical $X_2$ which can be split leaving behind a negatively charged oxygen atom is also acyloxy. Acyloxy is, for example, alkanoyloxy, such as lower alkanoyloxy, for example propionyloxy or especially acetoxy, and also aroyloxy, such as lower alkyl-benzoyloxy, for example methylbenzoyloxy, lower alkoxybenzoyloxy, for example methoxybenzoyloxy, halogenbenzoyloxy, for example chlorobenzoyloxy, especially benzoyloxy.

A radical $X_1$ or $X_2$ which can be detached leaving behind a carbonium ion is, especially, reactive esterified hydroxyl, such as hydroxyl esterified by a strong inorganic or organic acid, in particular a halogen atom, such as fluorine, chlorine, bromine or iodine. A hydroxyl $X_1$ esterified with an organic carboxylic acid is a hydroxyl group esterified with an organic sulphonic acid, such as an aromatic or aliphatic sulphonic acid, for example benzenesulphonic acid, 4-bromobenzenesulphonic acid, 4-toluenesulphonic acid or a lower alkane-sulphonic acid, for example methanesulphonic acid or ethanesulphonic acid. Thus, $X_1$ is, especially, benzenesulphonyloxy, 4-bromobenzenesulphonyloxy, 4-toluenesulphonyloxy, methanesulphonyloxy or ethanesulphonyloxy.

A radical $X_2$ which can be detached leaving behind a carbonium ion can also be free hydroxyl, a reactively esterified hydroxyl which differs from halogen or reactive etherified hydroxyl, or $X_2$ together with $R_2°$ forms epoxy or an ylidenedioxy radical. A hydroxyl $X_2$ esterified in this way is, especially, a hydroxyl group esterified by a strong inorganic or organic acid, such as sulphuric acid or a loweralkane-carboxylic acid, such as propionic acid or, in particular, acetic acid, or an arylcarboxylic acid, such as benzoic acid, or a halogenobenzoic acid, for example chlorobenzoic acid. Thus, $X_2$ is, especially, benzyloxy or propionyloxy or, in particular, acetoxy. A reactively etherified hydroxyl group is, for example, cycloalkoxy, such as cyclohexyloxy, aryl-lower alkoxy, such as benzyloxy, or, in particular, alkoxy, such as lower alkoxy, for example methoxy or ethoxy.

Particularly suitable radicals $X_2$ which can be detached leaving behind a carbonium ion are hydroxyl, methoxy, ethoxy, epoxy formed together with $R_2°$ and also, especially, halogen or lower alkanoyloxy, for example acetoxy.

Particularly suitable radicals $X_1$ which can be detached leaving behind a carbonium ion are halogen or sulphonyloxy groups, such as p-toluenesulphonyloxy.

A protective group $R_2°$, $R_3°$ and $R_4°$ is, for example, an easily splittable etherified or esterified hydroxyl group, such as a hydroxyl group etherified by lower alkenyl, especially allyl or propenyl, 1-alkoxy-alkyl, such as 1-ethoxy-ethyl, tetrahydropyranyl or tetrahydrofuranyl, or a hydroxyl group esterified by acyl, such as lower alkanoyl, for example acetyl, or aroyl, especially benzoyl, or lower alkyl-benzoyl, for example methylbenzoyl, lower alkoxy-benzoyl, for example methoxybenzoyl, or halogenobenzoyl, for example chlorobenzoyl.

Two of the radicals $R_2°$, $R_3°$ and $R_4°$ can, as a protective group, also conjointly be an ylidenedioxy group, such as an alkylidenedioxy group, for example a propylidenedioxy group, a cycloalkylidenedioxy group, for example a cyclopentylidene- or cyclohexylidenedioxy group, or an aralkylidenedioxy group, for example a benzylidenedioxy group, or can be in the form of the epoxy group.

The treatment of a compound of the formula (III) with an acid or base is effected especially with a Lewis acid, a strong inorganic acid or an inorganic or organic base.

Lewis acids are electron acceptors, for example those in which one atom possesses fewer electrons than a complete octet, such as boron tri-lower alkyl, for example boron trimethyl, or especially boron trihalides, such as boron trifluoride, boron trichloride or boron tribromide. Suitable Lewis acids are however, in particular, also metal halides in which the metal atom can accept more than eight outer electrons, such as titanium tetrahalides, niobium pentahalides or tantalum pentahalides, for example titanium tetrachloride, niobium pentachloride or tantalum pentachloride, or, in particular, tin dihalides, zinc dihalides and very particularly tin tetrahalides, for example tin dichloride, zinc dichloride and, in particular, tin tetrachloride.

Suitable strong inorganic acids are, for example, hydrogen halide acids, especially hydrofluoric acid.

Suitable inorganic bases are, especially, alkali metal hydroxides or alkaline earth metal hydroxides or corresponding carbonates or bicarbonates, such as sodium hydroxide, potassium hydroxide or, especially, barium hydroxide or sodium bicarbonate. Suitable organic bases are, especially, alkali metal alcoholates, such as alkali metal lower alkanolates, for example sodium ethylate, potassium tertiary butylate or, in particular, sodium methylate, and also nitrogen bases, such as, especially, sterically hindered nitrogen bases, for example tertiary amines or quaternary ammonium bases of tertiary amines, such as trilower alkyl-amines, for example triethylamine or, especially, trimethylamine, or a trilower alkyl-ammonium hydroxide, for example triethylammonium hydroxide or, especially, trimethylammonium hydroxide, or also aromatic nitrogen heterocyclic compounds, such as quinoline or pyridine. Basic ion exchangers, such as "Dowex 1"—a quaternary benzyltriethylammonium polystyrene—can also be used as bases.

If the compounds of the formula (III) are those in which one of the radicals $X_1$ and $X_2$ is hydroxyl and the other is halogen, the treatment can advantageously be carried out with an acid or base. If $X_1$ is hydroxyl and $X_2$ is halogen, suitable acids are, for example, hydrofluoric acid or especially Lewis acids and suitable bases are, for example, sterically hindered organic nitrogen bases. If $X_1$ is halogen and $X_2$ is hydroxyl, suitable bases are, for example, inorganic or organic bases or also strongly basic ion exchangers.

If $X_1$ is a radical which can be split leaving behind a negatively charged oxygen atom and which differs from hydroxyl and halogen and $X_2$ is a radical which can be detected leaving behind a carbonium ion, the treatment is carried out with acids, such as with strong inorganic acids or Lewis acids. This reaction can be carried out in a manner which is known per se with cooling, for example at $-10°$ C. to about $+10°$ C., or at room temperature, i.e. at about $+20°$ C. In order to accelerate the reaction, the reaction mixture can also be warmed slightly, for example to about 40° C. The reaction is advantageously carried out in a solvent, appropriately in halogenated hydrocarbons, such as in halogeno-lower alkanes, for example methylene chloride, chloroform or, especially, dichloroethane, or in aromatic compounds, such as toluene or xylene, preferably with the exclusion of water.

If $X_1$ is a radical which can be detached leaving behind a carbonium ion and if $X_2$ is a radical which can be split leaving behind a negatively charged oxygen atom and which differs from hydroxyl or halogen, the treatment is preferably carried out with bases, such as with inorganic or organic bases. This reaction can be carried out in a manner which is known per se with cooling, for example at $-10°$ C. to about $+10°$ C., or at room temperature, i.e. at about $+20°$ C. In order to accelerate the reaction, the reaction mixture can also be warmed slightly, for example to about 40°–60°. The treatment is advantageously carried out in a solvent, appropriately in water, in alcohols, such as a lower alkanol, for example methanol or ethanol, or in ethers, such as dimethyl ether, dioxane or tetrahydrofurane, or in acetone.

The detaching of a protective group, such as propenyl or tetrahydropyranyl, and especially of an ylidene radical, is generally effected by treatment with water or a lower alkanol, lower alkenol or aryl-lower alkanol in the presence of an acid.

The acid used is customarily a proton-acid, especially an inorganic acid, such as a mineral acid, for example a hydrogen halide acid, especially hydrochloric acid and also hydrobromic acid, and also sulphuric acid or phosphoric acid, or an organic acid, such as an organic carboxylic acid, for example formic acid or oxalic acid, or an organic sulphonic acid, for example p-toluenesulphonic acid, or a mixture of acids, for example a mixture of hydrochloric acid or p-toluenesulphonic acid and acetic acid, preferably in the form of glacial acetic acid, and also a salt having acid character.

Detaching is preferably carried out in the presence of a diluent and it is possible for a reactant, such as an alcoholic reagent or an organic acid, such as acetic acid, at the same time also to serve as the diluent; a mixture of solvents or diluents can also be used. If an alcohol is used the reaction is preferably carried out in the presence of a hydrogen halide acid, especially hydrochloric acid, and if water is used the reaction is preferably carried out in the presence of an organic carboxylic acid, especially formic acid or oxalic acid and in particular in the presence of acetic acid, the reaction being carried out, if necessary, with cooling, but, in particular, at room temperature or at elevated temperature (for example at about 25° to about 150°), if appropriate in a closed vessel under pressure and/or in an inert gas atmosphere, such as a nitrogen atmosphere.

If, in the above detaching reaction, an alcohol is used as the reagent in the presence of an anhydrous acid, especially hydrogen chloride, one of the two hydroxyl groups which are jointly etherified by the ylidene radical, and especially that in the 1-position, can be etherified at the same time as it is set free. The detaching reaction can, therefore, at the same time be used to introduce a hydroxyl group, etherified in the indicated manner, into a compound which is obtainable according to the process and which, for example, does not yet contain the indicated etherified hydroxyl group.

The novel anhydropyranose derivatives can also be obtained by introducing into a compound of the formula IV

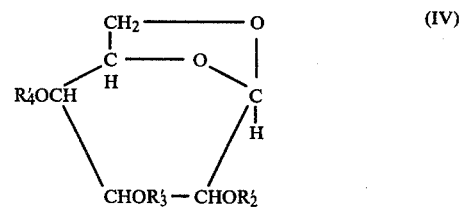

in which at least one of the radicals $R_2'$, $R_3'$ and $R_4'$ is hydrogen and the others are as defined as the $R_2$, $R_3$ or $R_4$, at least one radical $R_2$, $R_3$ and/or $R_4$, which differs from hydrogen.

Thus, a compound of the formula (IV) can be reacted with a reactive ester of an alkanol, alkenol or arylalkanol. A reactive ester of an alkanol, alkenol or arylalkanol is, especially, an ester with a strong inorganic or organic acid, such as, in particular, with a hydrogen halide acid, for example hydrochloric acid, hydrobromic acid or hydriodic acid, or sulphuric acid or with an organic sulphonic acid, such as with an aromatic or aliphatic sulphonic acid, for example benzenesulphonic acid, 4-bromobenzenesulphonic acid, 4-toluenesulphonic acid or a lower alkane-sulphonic acid, for example methanesulphonic acid or ethanesulphonic acid. Thus, an alkyl chloride, alkyl bromide or alkyl iodide, a benzenesulphonyloxyalkane, 4-bromobenzenesulphonyloxyalkane, 4-toluenesulphonyloxyalkane, methanesulphonyloxyalkane or ethanesulphonyloxyalkane or a corresponding derivative of an alkenol or arylalkanol is advantageously used for the reaction with a compound of the formula IV. The reaction is advantageously carried out in the presence of a basic agent, such as an alkali metal hydroxide, for example sodium hydroxide or potassium hydroxide, an alkali metal carbonate, such as sodium carbonate or potassium carbonate, or an alkali metal bicarbonate, such as sodium bicarbonate or potassium bicarbonate, or in the presence of silver oxide.

Furthermore, a compound of the formula IV in which at least one hydroxyl group has been converted into a reactive esterified hydroxyl group, especially into a halogen atom, such as bromine or iodine, or into a sulphonic acid ester, such as the tosylate or mesylate, can be reacted with an alkanol, alkenol or arylalkanol in the presence of a basic agent, such as the corresponding alkali metal alcoholate.

Furthermore, a compound of the formula IV in which the radicals $OR_2'$ and $OR_3'$, or $OR_3'$ and $OR_4'$, form an epoxy radical can be reacted with an alkanol, alkenol or arylalkanol in the presence of a suitable catalyst. Basic agents, for example a corresponding alkali metal alcoholate, for example a sodium alkanolate or potassium alkanolate, or acid agents, for example methanesulphonic acid or 4-toluenesulphonic acid, can be used as the catalyst.

Furthermore, it is possible to introduce an acyl radical $R_2$ or an aroyl radical $R_3$ or $R_4$ into a compound of the formula IV in which at least one hydroxyl group has been converted into a reactive esterified hydroxyl group, especially into a halogen atom, such as bromine or iodine, or into a sulphonic acid ester, such as the tosylate or mesylate. An acyl radical $R_2$ or an aroyl radical $R_3$ or $R_4$ can be introduced into a compound of the formula IV having free hydroxyl groups, especially according to acylation processes which are known per se, for example by reacting a compound of the formula IV with an acid corresponding to the acyl or aroyl radical, preferably with a corresponding reactive derivative thereof.

An acid derivative which is preferably used is, especially, an anhydride of a carboxylic acid, including a mixed anhydride, such as the anhydride with a hydrogen halide acid, for example hydrochloric acid, or the anhydride with a carbonic acid lower alkyl half-ester (which can be obtained, for example, by reacting a suitable salt, such as an ammonium salt, of the acid with a lower alkyl halogenoformate, for example ethyl chloroformate) or with a suitable, substituted or unsubstituted lower alkane-carboxylic acid, for example trichloroacetic acid or pivalic acid, and also an activated ester of such an acid, for example an ester with a N-hydroxyamino or N-hydroxyimino compound, such as N-hydroxy-succinimide, or with a lower alkanol containing electron-attracting groups, for example nitro, acyl, such as lower alkanoyl, for example acetyl, or aryl, for example benzoyl, groups, or free or functionally modified carboxyl groups, such as carbo-lower alkoxy groups, for example carbomethoxy or carboethoxy groups, carbamoyl groups, for example N,N-dimethylcarbamoyl groups, or cyano groups, especially methanol or phenol, for example cyanomethanol or 4-nitrophenol.

If necessary, the reaction is carried out in the presence of a suitable condensing agent and/or catalyst. An acid can be used, for example, in the presence of a dehydrating condensing agent, such as a carbodiimide, for example dicyclohexylcarbodiimide, and in the absence or presence of a catalyst, such as copper salt, for example copper-I chloride or copper-II chloride, or of a β-alkynylamine compound or lower alkoxyacetylene compound, an acid halide can be used, for example, in the presence of a basic, acid-binding condensing agent, such as pyridine or a tri-lower alkyl-amine, for example triethylamine, and an anhydride can be used, for example, in the presence of a suitable base, such as pyridine or a tri-lower alkyl-amine, or in the absence or presence of an acid catalyst, such as zinc chloride.

In resulting compounds it is possible, within the scope of the end products, to modify, introduce or detach substituents in the customary manner, or resulting compounds can be converted in the customary manner into other end products.

Thus, in resulting compounds which contain at least one free hydroxyl group, this group can be converted, especially as described above, into a radical $R_2$ and/or $R_4$ which differs from hydrogen.

Furthermore, in resulting compounds which contain at least one alkenyl radical $R_3$ or $R_4$, this radical can be hydrogenated, for example with hydrogen in the presence of a catalyst, such as with hydrogen in the presence of a palladium catalyst or platinum catalyst. Groups which are detachable by hydrogenolysis can be detached at the same time.

Furthermore, in resulting compounds which contain at least one detachable radical $R_2$ and/or $R_4$, this radical can be detached. Thus, it is possible, especially in resulting compounds which contain a radical detachable by solvolysis, to detach this radical by solvolysis, for example by hydrolysis or alcoholysis.

In a resulting compound having an acyl radical $R_2$ or aroyl radical $R_3$ and/or $R_4$ it is possible to convert an acyloxy or aroyloxy group into a hydroxyl group, for example by hydrolysis or by alcoholysis, preferably in the presence of a mild basic or acid agent. Such agents are, for example, basic agents such as ammonia, an alkali metal carbonate, an alkali metal hydroxide or alkoxides or acid agents such as an organic or inorganic acid, in the presence of, for example, aqueous or anhydrous alcohols or dioxane.

The novel compounds can be in the form of mixtures of diastereomers or in the form of the pure isomers. Resulting mixtures of isomers can be separated into the pure isomers by the known methods.

The processes described above are carried out according to methods which are known per se, in the absence or preferably in the presence of diluents or solvents, if necessary with cooling or warming, under elevated pressure and/or in an inert gas atmosphere, such as a nitrogen atmosphere.

Taking into account all of the substituents present in the molecule, particularly gentle reaction conditions, such as short reaction times, the use of mild acid or basic agents in low concentration, stoichiometric ratios and the choice of suitable catalyst, solvents and temperature and/or pressure conditions, are to be employed if necessary, especially if readily hydrolysable O-acyl radicals are present.

The invention also relates to those embodiments of the process in which a compound obtainable as an intermediate at any stage of the process is used as the starting material and the missing process steps are carried out, or the process is discontinued at any stage, or a starting material is formed under the reaction conditions or used in the form of a reactive derivative or salt. The starting materials used are preferably those which lead, according to the process, to the compounds described above as being particularly valuable.

The starting materials are known and/or can be prepared by methods which are known per se, for example by the cyclisation described above or by etherification or esterification of an anhydropyranose.

The present invention also relates to pharmaceutical formulations which contain compounds of the formula I. The pharmaceutical formulations according to the invention are those for enteral, such as oral or rectal, and also parenteral administration to warm-blooded animals and contain the pharmalogical active compound on its own or together with an excipient which can be used pharmaceutically. The dosage of the active compound depends on the species of warm-blooded animal, the age and the state of health of the individual and also on the mode of administration.

The novel pharmaceutical formulations contain from about 10% to about 95%, and preferably from about 20% to about 90%, of the active compound. Pharmaceutical formulations according to the invention can be in the form of dosage units, such as dragees, tablets, capsules, suppositories or ampoules.

The pharmaceutical formulations of the present invention are prepared in a manner which is known per se, for example by means of conventional mixing, granulating, dragée-making, dissolving or lyophilising processes. Thus, pharmaceutical formulations for oral use can be obtained by combining the active compound with solid excipients, granulating a resulting mixture if desired and processing the mixture or granules, after adding suitable auxiliaries if desired or necessary, to give tablets or dragée cores.

Suitable excipients are, especially, fillers, such as sugars, for example lactose or sucrose, mannitol or sorbitol, cellulose formulations and/or calcium phosphates, for example tricalcium phosphate or calcium hydrogen phosphate, as well as binders, such as starch paste using, for example, maize starch, wheat starch, rice starch or potato starch, gelatine, tragacanth, methylcellulose, hydroxypropyl-methylcellulose, sodium carboxymethyl cellulose and/or polyvinylpyrrolidone, and/or, if desired, disintegrating agents, such as the abovementioned starches, and also carboxymethylstarch, crosslinked polyvinylpyrrolidone, Agar or alginic acid or a salt thereof, such as sodium alginate. Auxiliaries are, in particular, flow-regulating agents and lubricants, for example silica, talc, stearic acid or salts thereof, such as magnesium stearate or calcium stearate, and/or polyethylene glycol. Dragée cores are provided with suitable coatings which, if desired, are resistant to gastric juices, and for this purpose, inter alia, concentrated sugar solutions, which can contain gum arabic, talc, polyvinylpyrrolidone, polyethylene glycol and/or titanium dioxide, lacquer solutions in suitable organic solvents or solvent mixtures or, in order to produce coatings resistant to gastric juices, solutions of suitable cellulose formulations, such as acetylcellulose phthalate or hydroxypropylmethylcellulose phthalate, are used. Dyestuffs or pigments can be added to the tablets or dragée coatings, for example for identification or in order to characterise different active compound doses.

Other pharmaceutical formulations which can be used orally are push-fit capsules made of gelatine, as well as soft, sealed capsules made of gelatine and plasticiser, such as glycerol or sorbitol. The push-fit capsules can contain the active compound in the form of granules, for example mixed with fillers, such as lactose, binders, such as starches, and/or lubricants, such as talc or magnesium stearate, and, if appropriate, stabilisers. In soft capsules, the active compound is preferably dissolved or suspended in suitable liquids, such as fatty oils, liquid paraffin or liquid polyethylene glycols, it also being possible to add stabilisers.

Possible pharmaceutical formulations which can be used rectally are, for example, suppositories, which consist of a combination of the active compound with a suppository base. Suitable suppository bases are, for example, natural or synthetic triglycerides, paraffin hydrocarbons, polyethylene glycols or higher alkanols. In addition it is also possible to use gelatine rectal capsules which consist of a combination of the active compound with a base; possible bases are, for example, liquid triglycerides, polyethylene glycols or paraffin hydrocarbons.

Formulations suitable for parenteral administration are, in particular, aqueous solutions of an active compound in the water-soluble form, for example of a water-soluble salt, and also suspensions of the active compound, such as corresponding oily injection suspensions, in which case suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and can also contain stabilisers.

The invention also relates to the treatment of warm-blooded animals in order to achieve fibrinolytic, thrombolytic and/or anti-inflammatory action by administering a pharmaceutical formulation according to the invention. The daily dose for a warm-blooded animal weighing about 70 kg is advantageously about 10–300 mg per day and preferably about 50–200 mg per day.

The examples which follow illustrate the invention described above; however, they are not intended to restrict the scope of the invention in any way. Temperatures are given in degrees Centigrade.

EXAMPLE 1

A solution of 13.6 g of 1,6-anhydro-3,4-di-O-benzyl-2-O-propenyl-β-D-galactopyranose in 200 ml of acetone is warmed with 10 ml of 1 N hydrochloric acid to 50° for 30 minutes. This mixture is neutralised with 10 ml of 1 N sodium hydroxide solution and the solution is evaporated under a water pump vacuum. The residue is taken up in ether and the organic phase is washed with water and dried over magnesium sulphate and the solvent is evaporated. After recrystallising once from ether/petroleum ether, the residue is 1,6-anhydro-3,4-di-O-benzyl-β-D-galactopyranose with a melting point of 69°–71°, an optical rotation $[\alpha]_D^{20}$ of $-38° \pm 1°$ (chloroform, c=1.123) and a Rf value of 0.25 on silica gel thin layer plates in the system methylene chloride/ethyl acetate (85/15).

1,6-Anhydro-3,4-di-O-benzyl-2-O-propenyl-β-D-galactopyranose, which is used as the starting material, can be prepared as follows.

A solution of 330 g of 3-O-benzyl-1,2;5,6-di-O-isopropylidene-α-D-glucofuranose in 3 l of ethanol and 200 ml of 7 N alcoholic hydrochloric acid are kept at 60° for 5 hours and the mixture is then freed from the bulk of the alcoholic hydrochloric acid under a water pump vacuum. The crystalline residue is taken up in methylene chloride, the solution is washed with a saturated solution of sodium bicarbonate and water and dried over magnesium sulphate and the solvent is evaporated. The product is crystallised from ethyl acetate. This gives ethyl-3-O-benzyl-α-D-glucopyranoside with a melting point of 127°–128°, a Rf value of 0.30 on silica gel thin layer plates in the system methylene chloride/methanol (15/1) and an optical rotation $[\alpha]_D^{20}$ of +86°±1° (chloroform, c=1.068).

A suspension of 52 g of ethyl-3-O-benzyl-α-D-glucopyranoside in 150 ml of benzaldehyde, which has been warmed to 50°–60°, is treated with 30 g of anhydrous zinc(II) chloride and the mixture is shaken vigorously. A clear solution is obtained and this solidifies after a short time. The reaction mixture is left to stand for 16 hours at about 25° and is then treated with 200 ml of ice-water and 400 ml of petroleum ether, while stirring. The crystals are filtered off, washed with water and petroleum ether, dried and recrystallised from boiling ethanol. This gives ethyl-3-O-benzyl-4,6-O-benzylidene-α-D-glucopyranoside with a melting point of 181°, a Rf value of 0.41 on silica gel thin layer plates in the system methylene chloride/ethyl acetate (85/15) and an optical rotation $[\alpha]_D^{20}$ of +68°±1° (chloroform, c=1.086).

120 g of ethyl-3-O-benzyl-4,6-O-benzylidene-α-D-glucopyranoside are dissolved in 500 ml of dimethylsulphoxide at 60° in a 750 ml sulphonation flask fitted with a stirrer, a condenser, a calcium chloride tube, a thermometer and a 50 ml dropping funnel and the solution is treated, while stirring in a nitrogen atmosphere, with 40 g of potassium hydroxide powder. 45 g of allyl bromide are now added dropwise in the course of 3 hours and the mixture is stirred for a further hour at 60°. After cooling, the reaction mixture is poured into ice-water. The resulting mixture is extracted with ether, the ether phase is washed with water until neutral and dried over magnesium sulphate and the solvent is evaporated. After recrystallising once from n-hexane, ethyl-2-O-allyl-3-O-benzyl-4,6-O-benzylidene-α-D-glucopyranoside with a melting point of 54°–55°, a Rf value of 0.66 on silica gel thin layer plates in the system methylene chloride/ethyl acetate, 85/15, and an optical rotation $[\alpha]_D^{20}$ of +14.5°±0.5° (chloroform, c=0.96) is obtained.

A solution of 52 g of ethyl-2-O-allyl-3-O-benzyl-4,6-O-benzylidene-α-D-glucopyranoside in 500 ml of ethanol and 50 ml of 1 N hydrochloric acid are kept at 60° for one hour. After cooling the reaction mixture, the latter is neutralised with 50 ml of 1 N sodium hydroxide solution and evaporated to dryness.

200 ml of water are added to the residue and the mixture is evaporated under a water pump vacuum. The residue, which is free from benzaldehyde, is taken up in methylene chloride and, after washing with water and drying over magnesium sulphate, freed from the solvent. This gives ethyl-2-O-allyl-3-O-benzyl-α-D-glucopyranoside in the form of a yellowish oil with a Rf value of 0.05 on silica gel thin layer plates in the system methylene chloride/ethyl acetate, 85/15, and an optical rotation $[\alpha]_D^{20}$ of +97°±1° (chloroform, c=1.472).

A solution of 50 g of ethyl-2-O-allyl-3-O-benzyl-α-D-glucopyranoside in 160 ml of pyridine is treated with 42 g of trityl chloride and the mixture is left to stand for 48 hours at about 25°. 2 ml of water are added and the bulk of the pyridine is evaporated under a water pump vacuum. The residue is treated with ether and water and the organic phase is washed twice more with water and dried over magnesium sulphate and the solvent is evaporated. 500 ml of toluene are added and the mixture is evaporated to dryness, this operation being repeated twice. This gives ethyl-2-O-allyl-3-O-benzyl-6-O-trityl-α-D-glycopyranoside in the form of a yellow oil with a Rf value of 0.39 on silica gel thin layer plates in the system ether/petroleum ether, 1/1.

A solution of 46.8 g of ethyl-2-O-allyl-3-O-benzyl-6-O-trityl-α-D-glucopyranoside in 100 ml of pyridine is treated dropwise, while stirring, with 10 ml of mesyl chloride in the course of 30 minutes and the mixture is left to stand for 24 hours at about 25°. The reaction mixture is poured into 500 ml of ice-water and extracted with 1 l of ether. The ether phase is washed with ice-cold 2 N hydrochloric acid, water, a saturated solution of sodium bicarbonate and water and dried over magnesium sulphate and the solvent is evaporated. The residue is crystallised from ethanol. This gives ethyl-2-O-allyl-3-O-benzyl-4-O-mesyl-6-O-trityl-α-D-glucopyranoside with a melting point of 142°, a Rf value of 0.51 on silica gel thin layer plates in the system methylene chloride and an optical rotation $[\alpha]_D^{20}$ of +49°±1° (chloroform, c=1.105).

A solution of 40 g of ethyl-2-O-allyl-3-O-benzyl-4-O-mesyl-6-O-trityl-α-D-glucopyranoside in 800 ml of N,N-dimethylformamide is stirred with 40 g of potassium acetate for 48 hours at 140°. The reaction mixture is cooled and filtered and the solvent is distilled off under a water pump vacuum. The residue in the flask is treated with water and ether, the organic phase is washed with water and dried over magnesium sulphate and the solvent is evaporated. The residue is dissolved in 400 ml of absolute methanol and the solution is treated with a solution of 0.5 g of sodium in 100 ml of methanol. After 20 hours at about 25°, the solvent is distilled off and the residue is taken up in ether. This solution is washed with water until neutral, dried over magnesium sulphate and evaporated to dryness. The product is purified by column chromatography on 1,200 g of silica gel using methylene chloride as the eluent. This gives ethyl-2-O-allyl-3-O-benzyl-6-O-trityl-α-D-galactopyranoside in the form of a yellowish oil with a Rf value of 0.13 on silica gel thin layer plates in the system methylene chloride.

A solution of 47.3 g of ethyl-2-O-allyl-3-O-benzyl-6-O-trityl-α-D-galactopyranoside in 200 ml of dimethylsulphoxide is treated with 30 g of potassium hydroxide powder, while stirring and with the exclusion of moisture, in a nitrogen atmosphere, and the mixture is warmed to 55°–60°. A solution of 12 g of benzyl chloride in 50 ml of dimethylsulphoxide is now added dropwise in the course of 5 hours and the reaction mixture is then stirred for a further 2 hours and poured into ice-water. The mixture is extracted with ether, the ether solution is washed with water until neutral and dried over magnesium sulphate and the solvent is evaporated. This gives ethyl-2-O-allyl-3,4-di-O-benzyl-6-O-trityl-α-D-galactopyranoside in the form of a yellowish oil with a Rf value of 0.46 on silica gel thin layer plates in the system methylene chloride.

A solution of 26.5 g of ethyl-2-O-allyl-3,4-di-O-benzyl-6-O-trityl-α-D-galactopyranoside in 2.7 l of benzene is boiled under reflux with 26.5 g of p-toluenesulphonic acid monohydrate for 20 minutes, while stirring. After cooling, this solution is washed with water, a saturated solution of sodium bicarbonate and water, dried over magnesium sulphate and evaporated to dryness. The residue is purified by column chromatography on 1,200 g of silica gel using ether/petroleum ether (1/1). This gives 1,6-anhydro-2-O-allyl-3,4-di-O-benzyl-β-D-galactopyranose in the form of a colourless oil with a Rf value of 0.28 on silica gel thin layer plates in the system ether/petroleum ether, 1/1, a boiling point of 175°/0.03 mm Hg and an optical rotation $[\alpha]_D^{20}$ of $-35°\pm1°$ (chloroform, c=1.151).

A solution of 15.7 g of 1,6-anhydro-2-O-allyl-3,4-di-O-benzyl-β-D-galactopyranose in 80 ml of dimethylsulphoxide is stirred with 2.4 g of potassium tert.-butylate for 30 minutes at 100° in a nitrogen atmosphere. The mixture is cooled, poured into ice-water and extracted with ether. The ether phase is washed with water, dried over magnesium sulphate and concentrated to about 30 ml. This solution is introduced onto 50 g of neutral aluminium oxide of activity stage I, which is in a chromatography column, and the product is eluted with ether. This gives 1,6-anhydro-3,4-di-O-benzyl-2-O-propenyl-β-D-galactopyranose in the form of a yellow oil with a Rf value of 0.41 on silica gel thin layer plates in the system ether/petroleum ether (1/1).

EXAMPLE 2

A solution of 25.3 g of 1,6-anhydro-3,4-di-O-benzyl-2-O-propenyl-β-D-glucopyranose in 200 ml of acetone is treated with 10 ml of 1 N hydrochloric acid and the mixture is kept at 50° for 30 minutes. The solution is cooled, neutralised with 1 N sodium hydroxide solution and evaporated to dryness. The residue is taken up in ether and the solution is washed with water, dried over magnesium sulphate and freed from the solvent. The residue is purified by column chromatography on 1 kg of silica gel using ether/petroleum ether (1/1). This gives 1,6-anhydro-3,4-di-O-benzyl-β-D-glucopyranose in the form of a yellowish oil with a Rf value of 0.10 on silica gel thin layer plates in the system ether/petroleum ether (1/1) and an optical rotation $[\alpha]_D^{20}$ of $-36°\pm1°$ (chloroform, c=0.955).

The starting material used can be prepared as follows.

A solution of 44.7 g of ethyl-2-O-allyl-3-O-benzyl-6-O-trityl-β-D-glucopyranoside in 100 ml of dimethylsulphoxide in 100 ml of dimethylsulphoxide is treated with 10 g of potassium hydroxide powder, while stirring and with the exclusion of moisture, in a nitrogen atmosphere, and the mixture is warmed to 60°. A solution of 10.8 g of benzyl chloride in 20 ml of dimethylsulphoxide is now added dropwise in the course of 6 hours and the mixture is then stirred for a further 2 hours at 60°. This batch is cooled and poured into ice-water. It is extracted with ether and the organic phase is washed with water until neutral, dried over magnesium sulphate and evaporated to dryness. This gives ethyl-2-O-allyl-3,4-di-O-benzyl-6-O-trityl-α-D-glucopyranoside in the form of a yellow oil with a Rf value of 0.55 on silica gel thin layer plates in the system ether/petroleum ether (1/1).

A solution of 62 g of ethyl-2-O-allyl-3,4-di-O-benzyl-6-O-trityl-α-D-glucopyranoside in 3.1 l of benzene is stirred under reflux with 31 g of p-toluenesulphonic acid monohydrate for 30 minutes. After cooling, this solution is washed with 230 ml of 1 N sodium hydroxide solution and water, dried over magnesium sulphate and evaporated to dryness. The residue is purified by column chromatography on 1 kg of neutral aluminium oxide of activity stage I using methylene chloride as the eluent. This gives 1,6-anhydro-2-O-allyl-3,4-di-O-benzyl-β-D-glucopyranose with a Rf value of 0.26 on silica gel thin layer plates in the system ether/petroleum ether (1/1), a boiling point of 175°/0.03 mm Hg and an optical rotation $[\alpha]_D^{20}$ of $-19°\pm1°$ (chloroform, c=1.019).

A solution of 29.5 g of 1,6-anhydro-2-O-allyl-3,4-di-O-benzyl-β-D-glucopyranose in 82 ml of dimethylsulphoxide is stirred with 4.3 g of potassium tert.-butylate for 30 minutes at 100° in a nitrogen atmosphere. After cooling, the reaction mixture is poured into ice-water and extracted with ether. The ether phase is washed with water, dried over magnesium sulphate and evaporated to dryness. This gives 1,6-anhydro-3,4-di-O-benzyl-2-O-propenyl-β-D-glucopyranose with a Rf value of 0.38 on silica gel thin layer plates in the system ether/petroleum ether (1/1).

EXAMPLE 3

A solution of 47.7 g of 1,6-anhydro-3,4-di-O-benzyl-β-D-glucopyranose in 250 ml of pyridine is treated dropwise with 18.5 ml of benzoyl chloride and the mixture is left to stand at about 25° for 16 hours. 10 ml of water are added and after 30 minutes the bulk of the pyridine is evaporated under a water pump vacuum. The residue in the flask is treated with ether and water and the ether phase is then washed with ice-cold 2 N hydrochloric acid, a dilute solution of sodium carbonate and water, dried over magnesium sulphate and evaporated to dryness. The product crystallises from ether/petroleum ether and is recrystallised from ethanol. This gives 1,6-anhydro-2-O-benzoyl-3,4-di-O-benzyl-β-D-glucopyranose with a melting point of 78°–79°, a Rf value of 0.28 on silica gel thin layer plates in the system ether/petroleum ether, 1/1, and an optical rotation $[\alpha]_D^{20}$ of $+9°\pm1°$ (chloroform, c=1.048).

EXAMPLE 4

A solution of 20.5 g of 1,6-anhydro-2-O-benzoyl-3,4-di-O-benzyl-β-D-glucopyranose in 300 ml of methanol and 50 ml of 1 N sodium hydroxide solution is left to stand for 18 hours at about 25° and is then evaporated to dryness under a water pump vacuum. The residue is taken up in ether, this solution is washed with water until neutral and dried over magnesium sulphate and the solvent is evaporated. This gives 1,6-anhydro-3,4-di-O-benzyl-β-D-glucopyranose in the form of a yellowish oil with a Rf value of 0.10 on silica gel thin layer plates in the system ether/petroleum ether (1/1) and an optical rotation $[\alpha]_D^{20}$ of $+37°\pm1°$ (chloroform, c=0.895).

EXAMPLE 5

A solution of 51 g of 1,6-anhydro-3,4-di-O-benzyl-2-O-tetrahydropyranyl-β-D-glucopyranose in 400 ml of acetone is warmed with 20 ml 1 N hydrochloric acid to 50° for 20 minutes. After cooling, this solution is neutralised with 1 N sodium hydroxide solution and evaporated to dryness. The residue is taken up in ether, this solution is washed thoroughly with water and dried over magnesium sulphate and the solvent is evaporated. The product is benzoylated as described in Example 3 and the 1,6-anhydro-2-O-benzoyl-3,4-di-O-benzyl-β-D- glucopyranose which is thus obtained is purified by recrystallisation.

The starting material used can be prepared as follows:

A solution of 50 g of 1,6:3,4-dianhydro-2-O-tetrahydropyranyl-β-D-galactopyranose in 400 ml of dioxane is treated with 400 ml of 5% potassium hydroxide solution and the mixture is boiled under reflux for 48 hours. The batch is cooled and treated with 750 ml of ether. The aqueous phase is separated off and washed once more with 250 ml of ether, treated with 19.5 g of ammonium chloride and evaporated to dryness. The residue is extracted with methylene chloride and the solvent is distilled off. This gives 1,6-anhydro-2-O-tetrahydropyranyl-β-D-glucopyranose in the form of white crystals with a melting point of 111°–113° and a Rf value of 0.17 on silica gel thin layer plates in the system ethyl acetate.

A solution of 31.6 g of 1,6-anhydro-2-O-tetrahydropyranyl-β-D-glucopyranose in 150 ml of dimethylsulphoxide is treated with 25 g of potassium hydroxide powder, while stirring and with the exclusion of moisture, in a nitrogen atmosphere, and the mixture is warmed to 55°–60°. 33 ml of benzyl chloride are now added dropwise in the course of 6 hours and the mixture is stirred for a further two hours at 60°. After cooling, the reaction mixture is poured into 500 ml of ice-water and extracted with ether. The ether phase is washed with water until neutral, dried over magnesium sulphate and concentrated to about 100 ml. This solution is filtered through 200 g of basic aluminium oxide and the product is eluted with ether. After evaporating the eluate, 1,6-anhydro-3,4-di-O-benzyl-2-O-tetrahydropyranyl-β-D-glucopyranose is obtained in the form of a yellow oil with a Rf value of 0.49 on silica gel thin layer plates in the system methylene chloride/ethyl acetate (85/15).

EXAMPLE 6

A solution of 57.8 g of 1,2,4-tri-O-acetyl-3-O-benzyl-6-O-trityl-D-glucopyranose in 900 ml of 1,2-dichloroethane is stirred under reflux with 23.7 g of dry zinc-II chloride for 18 hours. After cooling, the reaction mixture is filtered and the filtrate is washed with water, a saturated solution of sodium bicarbonate and water, dried over magnesium sulphate and evaporated to dryness. The residue is dissolved in 500 ml of methanol and the solution is treated with 2 g of sodium carbonate, stirred for 3 hours at about 25° C. and evaporated to dryness under a water pump vacuum. The residue is taken up in water, the mixture is freed from insoluble material by filtration and the filtrate is extracted three times wth methylene chloride. The organic phase is dried over magnesium sulphate and evaporated and the residue is purified on 250 g of silica gel, using ethyl acetate as the eluent. This gives 1,6-anhydro-3-O-benzyl-β-D-glucopyranose in the form of a yellowish oil with a Rf value of 0.32 on silica gel thin layer plates in the system ethyl acetate and an optical rotation $[\alpha]_D^{20}$ of $-51° \pm 1°$ (chloroform, c=1.398).

EXAMPLE 7

A solution of 63.8 g of 1,6-anhydro-3-O-benzoyl-4-O-benzyl-2-O-tetrahydropyranyl-β-D-glucopyranose in 500 ml of ethanol is treated with 50 ml of 1 N hydrochloric acid and the mixture is kept at 50° C. for 30 minutes. After cooling, the solution is neutralised with 40 ml of 1 N sodium hydroxide solution and solid sodium bicarbonate and evaporated to dryness. The residue is partitioned between ether and water and the organic phase is evaporated after it has been dried over magnesium sulphate. The resulting 1,6-anhydro-3-O-benzoyl-4-O-benzyl-β-D-glucopyranose is crystallised from ether/petroleum ether; melting point 90°–92° C., $[\alpha]_D^{20} = -15° \pm 1°$ (chloroform, c=2.598) and Rf value 0.32 on silica gel thin layer plates in the system methylene chloride/ethyl acetate (85:15).

The starting material used can be prepared as follows:

A solution of 31.6 g of 1,6-anhydro-2-O-tetrahydropyranyl-β-D-glucopyranose in 150 ml of dimethylsulphoxide is treated with 25 g of potassium hydroxide powder, while stirring and with the exclusion of moisture, in a nitrogen atmosphere, and the mixture is warmed to 55°–60° C. A solution of 16.5 ml of benzyl chloride in 20 ml of dimethylsulphoxide is now added dropwise in the course of 5 hours and the resulting mixture is stirred for a further two hours at 60° C. After cooling, the reaction mixture is poured into 500 ml of ice-water and extracted with ether. The ether phase is washed with water until neutral, dried over magnesium sulphate and freed from the solvent. The residue is taken up in a little methylene chloride and introduced onto a chromatography column (silica gel, 1,200 g). Using methylene chloride/ethyl acetate (85:15), 1,6-anhydro-4-O-benzyl-2-O-tetrahydropyranyl-β-D-glucopyranose is eluted in the form of a pale yellow oil with a Rf value of 0.22 on silica gel thin layer plates in the system methylene chloride/ethyl acetate (85:15) and an optical rotation $[\alpha]_D^{20}$ of $+24° \pm 1°$ (chloroform, c=0.627).

A solution of 43.5 g of 1,6-anhydro-4-O-benzyl-2-O-tetrahydropyranyl-β-D-glucopyranose in 250 ml of absolute pyridine is treated dropwise with 18 ml of benzyl chloride, while stirring and with the exclusion of moisture, and the mixture is left to stand for 18 hours at about 22° C. 10 ml of ice-water are added, the resulting mixture is left to stand for about 30 minutes and the solvent is evaporated. The residue is taken up in ether and the ether solution is washed with water and dried over magnesium sulphate. After distilling off the solvent, this gives 1,6-anhydro-3-O-benzoyl-4-O-benzyl-2-O-tetrahydropyranyl-β-D-glucopyranose with a Rf value of 0.54 on silica gel thin layer plates in the system methylene chloride/ethyl acetate (85:15).

EXAMPLE 8

A solution of 21.9 g of 1,6-anhydro-4-O-benzoyl-3-O-benzyl-2-O-tetrahydropyranyl-β-D-gulopyranose in 100 ml of ethanol and 10 ml of 1 N hydrochloric acid is kept at 50° C. for 45 minutes. The reaction mixture is cooled, neutralised with 7 ml of 1 N sodium hydroxide solution and a saturated solution of sodium bicarbonate and evaporated. The residue is partitioned between ether and water and the ether phase is dried over magnesium sulphate and evaporated. 1,6-Anhydro-4-O-benzoyl-3-O-benzyl-β-D-gulopyranose is crystallised from ether/petroleum ether; melting point 92°–93° C., $[\alpha]_D^{20} = -14° \pm 1°$ (chloroform, c=1.317) and Rf value 0.37 on silica gel thin layer plates in the system methylene chloride/ethyl acetate (85:15).

The starting material used can be prepared as follows:

A solution of 1.5 g of sodium and 10 g of 1,6;3,4-dianhydro-2-O-tetrahydropyranyl-β-D-galactopyranose in 100 ml of benzyl alcohol is kept at 100° C. for 3 hours. After cooling, this solution is diluted with 500 ml of ether, washed with water until neutral, dried over magnesium sulphate and evaporated (finally under a high vacuum). The crude product is chromatographed on 500 g of silica gel using methylene chloride/ethyl acetate (85:15). In addition to 1,6-anhydro-4-O-benzyl-2-O-tetrahydropyranyl-β-D-glucopyranose (Rf value 0.33 in the system methylene chloride/ethyl acetate, 85:15), 1,6-anhydro-3-O-benzyl-2-O-tetrahydropyranyl-β-D-gulopyranose with a Rf value of 0.12 on silica gel thin layer plates in the system methylene chloride/ethyl acetate, 85:15, is eluted. This product is recrystallised from ether/petroleum ether; melting point 118°–119° C., $[\alpha]_D^{20} = -90° \pm 1°$ (chloroform, c=0.957).

A solution of 15.0 g of 1,6-anhydro-3-O-benzyl-2-O-tetrahydropyranyl-β-D-gulopyranose in 100 ml of absolute pyridine is treated dropwise with 6.25 ml of benzoyl chloride and the mixture is left to stand for 18 hours at about 22° C. 10 ml of ice-water are now added and the solvent is evaporated. The residue is taken up in ether, the ether solution is washed with water and dried over magnesium sulphate and the solvent is distilled off. This gives 1,6-anhydro-4-O-benzoyl-3-O-benzyl-2-O-tetrahydropyranyl-β-D-gulopyranose with a Rf value of 0.56 on silica gel thin layer plates in the system methylene chloride/ethyl acetate (85:15).

EXAMPLE 9

A solution of 11.6 g of 1,6-anhydro-3,4-di-O-benzyl-2-O-tetrahydropyranyl-β-D-gulopyranose in 50 ml of ethanol and 5 ml of 1 N hydrochloric acid is kept at 50° C. for 2 hours. The reaction mixture is cooled, neutralised with 5 ml of 1 N sodium hydroxide solution and evaporated. The residue is taken up in ether, the ether solution is washed with water and dried over magnesium sulphate and the filtrate is evaporated. The product is purified by column chromatography on 250 g of silica gel using methylene chloride/ethyl acetate (19:1) as the continuous phase. This gives 1,6-anhydro-3,4-di-O-benzyl-β-D-gulopyranose in the form of a pale yellow oil with a Rf value of 0.31 on silica gel thin layer plates in the system methylene chloride/ethyl acetate (85:15) and an optical rotation $[\alpha]_D^{20}$ of $-37° \pm 1°$ (chloroform, c=1.141).

The starting material used can be prepared as follows:

A solution of 10 g of 1,6-anhydro-3-O-benzyl-2-O-tetrahydropyranyl-β-D-gulopyranose in 20 ml of absolute dimethylsulphoxide is treated with 3 g of potassium hydroxide powder, while stirring and with the exclusion of moisture, in a nitrogen atmosphere, and the mixture is warmed to 50° C. A solution of 3.8 ml of benzyl chloride in 10 ml of dimethylsulphoxide is added dropwise at this temperature in the course of 3½ hours. After stirring for a further one hour, the reaction mixture is cooled, poured into ice-water and extracted with ethyl acetate. The organic phase is washed with water until neutral and dried over magnesium sulphate and the solvent is distilled off. The resulting 1,6-anhydro-3,4-di-O-benzyl-2-O-tetrahydropyranyl-β-D-gulopyranose is crystallised from ethyl acetate/petroleum ether; melting point 98°–99° C., Rf value 0.47 on silica gel thin layer plates in the system methylene chloride/ethyl acetate (85:15).

EXAMPLE 10

A solution of 17 g of 1,6-anhydro-4-O-benzyl-3-O-propyl-2-O-tetrahydropyranyl-β-D-glucopyranose in 100 ml of ethanol and 10 ml of 1 N hydrochloric acid is kept at 50° C. for 1 hour. After cooling and neutralising the solution with sodium hydroxide solution, the solvent is evaporated under a water pump vacuum. The residue is partitioned between ether and water and the organic phase is dried over magnesium sulphate and evaporated. The product is purified by column chromatography on 500 g of silica gel using methylene chloride/ethyl acetate (85:15) as the continuous phase. This gives 1,6-anhydro-4-O-benzyl-3-O-propyl-β-D-glucopyranose in the form of a pale yellow oil with a Rf value of 0.25 on silica gel thin layer plates in the system methylene chloride/ethyl acetate, 85/15, and an optical rotation $[\alpha]_D^{20}$ of $-40° \pm 1°$ (chloroform, c=1.178).

The starting material can be prepared as follows:

A solution of 17 g of 1,6-anhydro-4-O-benzyl-2-O-tetrahydropyranyl-β-D-glucopyranose in 50 ml of dimethylsulphoxide is treated with 4.6 g of potassium hydroxide powder, while stirring and with the exclusion of moisture, in a nitrogen atmosphere, and the mixture is warmed to 50° C. A solution of 5 ml of propyl bromide in 10 ml of dimethylsulphoxide is added dropwise at this temperature in the course of 4 hours and the mixture is stirred for a further 10 hours at this temperature. A further 3.2 g of potassium hydroxide powder are added, 25 ml of propyl bromide in 5 ml of dimethylsulphoxide are added dropwise and the mixture is stirred for 10 hours. After cooling, the reaction mixture is poured into ice-water and extracted with ether. The ether phase is washed with water until neutral, dried over magnesium sulphate and evaporated. The yellow oil is 1,6-anhydro-4-O-benzyl-3-O-propyl-2-O-tetrahydropyranyl-β-D-glucopyranose with a Rf value of 0.40 on silica gel thin layer plates in the system methylene chloride/ethyl acetate, 85:15.

EXAMPLE 11

A solution of 11.3 g of 1,6-anhydro-3-O-benzyl-4-O-propyl-2-O-tetrahydropyranyl-β-D-gulopyranose in 50 ml of ethanol and 5 ml of 1 N hydrochloric acid is kept at 50° C. for 2 hours. This solution is cooled, neutralised with sodium hydroxide solution and evaporated to dryness. The residue is partitioned between ether and water and the organic phase is dried over magnesium sulphate, filtered and evaporated. The product is purified by column chromatography on 100 g of silica gel using methylene chloride/ethyl acetate (85:15) as the continuous phase. This gives 1,6-anhydro-3-O-benzyl-4-O-propyl-β-D-gulopyranose with a Rf value of 0.33 on silica gel thin layer plates in the system methylene chloride/ethyl acetate, 85:15, and an optical rotation $[\alpha]_D^{20}$ of $-36° \pm 1°$ (chloroform, c=0.612).

The starting material can be prepared as follows:

A solution of 10 g of 1,6-anhydro-3-O-benzyl-2-O-tetrahydropyranyl-β-D-gulopyranose in 20 ml of absolute dimethylsulphoxide is treated with 3 g of potassium hydroxide powder, while stirring and with the exclusion of moisture, in a nitrogen atmosphere, and the mixture is warmed to 50° C. A solution of 3 ml of propyl bromide in 10 ml of dimethylsulphoxide is added dropwise at this temperature in the course of 2 hours and the reaction mixture is stirred for a further 3 hours. A further 3 g of potassium hydroxide powder are added, a solution of 3 ml of propyl bromide in 10 ml of dimethylsulphoxide is added dropwise and the mixture is stirred for 2 hours. The reaction mixture is now cooled and poured into ice-water. The resulting mixture is extracted with ether and the ether phase is washed with water until neutral and dried over magnesium sulphate. After evaporating off the solvent, 1,6-anhydro-3-O-benzyl-4-O-propyl-2-O-tetrahydropyranyl-β-D-gulopyranose is obtained in the form of yellow oil with a Rf value of 0.42 on silica gel thin layer plates in the system methylene chloride/ethyl acetate, 85:15.

EXAMPLE 12

A solution of 13.5 g of 1,6-anhydro-3,4-di-O-benzyl-β-D-mannopyranose in 150 ml of pyridine is treated dropwise with 5 ml of benzoyl chloride, with the exclusion of moisture, and the mixture is left to stand for 18 hours at about 22° C. 10 ml of ice-water are now added and the bulk of the pyridine is evaporated. The residue is taken up in ether and this solution is washed with water, ice-cold 2 N hydrochloric acid, water, a saturated solution of sodium bicarbonate and water and dried over magnesium sulphate and the solvent is evaporated. The 1,6-anhydro-2-O-benzoyl-3,4-di-O-benzyl-β-D-mannopyranose, which has remained behind, is crystallised from ether/petroleum ether; melting point 72.5°–73° C., Rf value 0.15 on silica gel thin layer plates in the system methylene chloride, $[\alpha]_D^{20} = +58° \pm 1°$ (chloroform, c=1.123).

The starting material can be prepared as follows.

A solution of 17 g of 1,6-anhydro-3,4-di-O-benzyl-β-D-glucopyranose in 150 ml of absolute dimethylformamide and 14.2 ml of absolute dimethylsulphoxide is treated with 14.2 g of phosphorus pentoxide in portions, while stirring and with the exclusion of moisture. This reaction mixture is now stirred for 4 hours at 60° C., cooled and poured into 250 ml of a saturated solution of sodium bicarbonate. The mixture is extracted with chloroform, the organic phase is washed with water and dried over magnesium sulphate and the solvent is evaporated. The resulting 1,6-anhydro-3,4-di-O-benzyl-β-D-arabino-hex-2-ulo-pyranose with a Rf value of 0.63 on silica gel thin layer plates in the system methylene chloride/ethyl acetate, 85:15, is dried under a high vacuum.

A solution of 15.2 g of 1,6-anhydro-3,4-di-O-benzyl-β-D-arabino-hex-2-ulo-pyranose in 150 ml of methanol is added dropwise in the course of 3 hours to a solution, which has been cooled to 0° C., of 2 g of sodium borohydride in 90 ml of methanol/water, 3:1. The mixture is stirred for a further 1 hour in an ice-bath, 30 ml of acetone are added and the solvent is evaporated. The residue is taken up in ether, the ether solution is washed with water and dried over magnesium sulphate and the solvent is evaporated. This gives 1,6-anhydro-3,4-di-O-benzyl-β-D-mannopyranose with a Rf value of 0.37 on silica gel thin layer plates in the system methylene chloride/ethyl acetate, 85:15.

We claim:

1. 1,6-Anhydro-β-D-hexopyranose derivatives of the formula

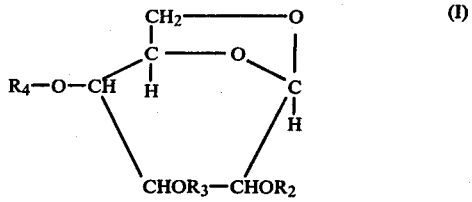

(I)

wherein $R_2$ is hydrogen, methyl, benzoyl, benzoyl substituted by halogen, lower alkyl, lower alkoxy, hydroxy or lower alkanoyl, or naphthoyl, one of the two radicals $R_3$ and $R_4$ is lower alkyl, phenyl-methyl, phenyl-methyl substituted by halogen, lower alkyl, lower alkoxy, hydroxy or lower alkanoyloxy, or naphthyl-methyl and the other is lower alkyl, phenyl-methyl, phenyl-methyl substituted by halogen, lower alkyl, lowr alkoxy, hydroxy or lower alkanoyloxy, naphthyl-methyl, benzoyl, benzoyl substituted by halogen, lower alkyl, lowr alkoxy, hydroxy or lower alkanoyloxy, or naphthoyl and $R_4$ can also be hydrogen, with the proviso that the radicals $R_3$ and $R_4$ together contain at least 3 carbon atoms, and when $R_4$ is benzyl, $R_3$ contains at least 2 carbon atoms, and when one of the radicals $R_3$ and $R_4$ is benzoyl, benzoyl substituted as defined above or naphthoyl, $R_2$ is hydrogen.

2. A compound of the formula

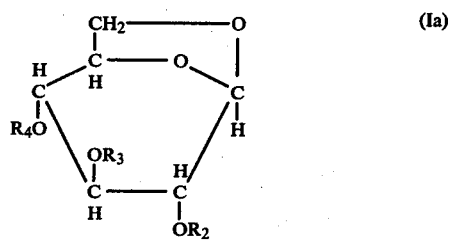

(Ia)

in which $R_2$, $R_3$ and $R_4$ are as defined in claim 1.

3. A compound of the formula (Ia) according to claim 2, in which $R_3$ is a benzyl radical and $R_2$ and $R_4$ are as defined in claim 2.

4. A compound of the formula (Ia) according to claim 2, in which $R_2$ is hydrogen or methyl, $R_3$ is a benzyl radical and $R_4$ is hydrogen or benzyl.

5. A compound of the formula (Ia) according to claim 2, wherein $R_3$ and $R_4$ are benzyl radicals, and $R_2$ is hydrogen or benzoyl.

6. A compound of the formula (Ia) according to claim 2, wherein $R_3$ is benzyl, and $R_2$ and $R_4$ are hydrogen.

7. A compound of the formula (Ia) according to claim 2, in which $R_2$ is hydrogen, benzoyl, benzoyl substituted by halogen, lower alkyl, lower alkoxy, hydroxy or lower alkanoyloxy, or naphthoyl, $R_3$ is lower alkyl, phenyl-methyl, phenyl-methyl substituted by halogen, lower alkyl, lower alkoxy, hydroxy or lower alkanoyloxy, or napthyl-methyl and $R_4$ is hydrogen, lower alkyl, phenyl-methyl, phenyl-methyl substituted by halogen, lower alkyl, lower alkoxy, hydroxy or lower alkanoyloxy, or naphthyl-methyl, benzoyl, benzoyl substituted by halogen, lower alkyl, lower alkoxy, hydroxy or lower alkanoyloxy, or naphthoyl, with the proviso that $R_3$ and $R_4$ together contain at least 3 carbon atoms and, when $R_4$ is benzyl, $R_3$ contains at least 2 carbon atoms and, when $R_4$ is benzoyl, benzoyl substituted as defined above or naphthoyl, $R_2$ is hydrogen.

* * * * *